United States Patent
Fahl (10) Patent No.: US 10,478,287 B2
(45) Date of Patent: Nov. 19, 2019

(54) SPEAKING VALVE WITH COVER PART, COMPRISING A CLOSURE PART WITH A RISING CENTRAL PART

(71) Applicant: Andreas Fahl Medizintechnik—Vertrieb GmbH, Cologne (DE)

(72) Inventor: Andreas Fahl, Köln (DE)

(73) Assignee: Andreas Fahl Medizintechnik—Vertrieb GmbH, Cologne (DE)

(*) Notice: Subject to any disclaimer, the term of this patent is extended or adjusted under 35 U.S.C. 154(b) by 21 days.

(21) Appl. No.: 15/565,545

(22) PCT Filed: Apr. 6, 2016

(86) PCT No.: PCT/EP2016/057489
§ 371 (c)(1),
(2) Date: Oct. 10, 2017

(87) PCT Pub. No.: WO2016/162365
PCT Pub. Date: Oct. 13, 2016

(65) Prior Publication Data
US 2018/0071083 A1    Mar. 15, 2018

(30) Foreign Application Priority Data
Apr. 10, 2015   (DE) .................. 10 2015 105 496

(51) Int. Cl.
*A61F 2/20*       (2006.01)
*A61M 16/04*   (2006.01)
(Continued)

(52) U.S. Cl.
CPC ............ *A61F 2/20* (2013.01); *A61M 16/0468* (2013.01); *A61M 16/0688* (2014.02); *A61M 16/1045* (2013.01)

(58) Field of Classification Search
CPC ...... A61F 2/20; A61F 2002/206; A61F 2/203; A61M 16/0468; A61M 16/0465
See application file for complete search history.

(56) References Cited

U.S. PATENT DOCUMENTS

| 4,582,058 A | 4/1986 | Depel et al. |
| 5,738,095 A * | 4/1998 | Persson ................... A61F 2/20 128/201.13 |

(Continued)

FOREIGN PATENT DOCUMENTS

| DE | 102012109916 A1 | 4/2014 |
| EP | 1077658 B1 | 9/2004 |

(Continued)

*Primary Examiner* — Thomas Sweet
*Assistant Examiner* — Rebecca Lynee Zimmerman
(74) *Attorney, Agent, or Firm* — Dinsmore & Shohl LLP (57) ABSTRACT

The invention relates to a speaking valve for laryngectomized or tracheotomized persons, comprising a cover part, a housing part, and a filter arranged in the housing part. The cover part comprises a closure part which is arranged on an inner face of the cover part and which faces the filter. The cover part consists of an elastic material, and the closure part closes the speaking valve distally to the filter by deforming at least one region of the cover part. The closure part has a circular shape and has a central part surface which rises starting from a lower end surface of an outer edge to a centrally arranged securing region.

18 Claims, 5 Drawing Sheets

(51) Int. Cl.
*A61M 16/06* (2006.01)
*A61M 16/10* (2006.01)

(56) References Cited

U.S. PATENT DOCUMENTS

2010/0288284 A1* 11/2010 Persson ............ A61M 16/0468
128/207.14
2011/0220108 A1* 9/2011 Persson ............ A61M 16/0468
128/205.29

FOREIGN PATENT DOCUMENTS

| WO | 9517138 A1 | 6/1995 |
|---|---|---|
| WO | 2008132222 A2 | 11/2008 |

* cited by examiner

SPEAKING VALVE WITH COVER PART, COMPRISING A CLOSURE PART WITH A RISING CENTRAL PART

CROSS-REFERENCE TO RELATED APPLICATIONS

This application is the U.S. national stage of PCT/EP2016/057489 filed Apr. 6, 2016, which claims priority of German Patent Application 10 2015 105 496.5 filed Apr. 10, 2015 of which is hereby incorporated by reference in its entirety.

FIELD OF THE INVENTION

The present disclosure relates to a speaking valve for laryngectomized or tracheostomized humans. The speaking valve has a cover part, a housing part and a filter.

BACKGROUND OF THE INVENTION

Speaking valves are known from the prior art. These are attached to a tracheostoma cannula or tracheostoma bandage, so that humans without vocal chords can speak by means of a voice prosthesis. Air is conducted through a voice prosthesis by actuating the speaking valve, which is disposed in a fistula between the trachea and esophagus. Even when the vocal chords are still present, it is necessary that the air not escape from the tracheal cannula before reaching the vocal chords.

It is known from U.S. Pat. No. 4,582,058 to close a speaking valve by means of a pressure impulse caused by the breathing of the patient, thereby enabling speech. These valves have proven to be not particularly reliable, however.

WO 95/17138 A1 proposes combining the speaking valve with an artificial nose. This artificial nose is a filter, which collects the moisture and heat of the exhaled air, and moisturizes and heats the air flowing into the trachea cannula.

EP 1 077 658 B1 describes a speaking valve with a filter, wherein the speaking valve has an elastic housing, or elastic valve element, and the housing or valve element can be deformed, e.g. by means of finger pressure, such that a housing part bears on a valve seat, formed in particular by a tracheal cannula or a tracheostoma bandage, thus closing the valve.

SUMMARY OF THE INVENTION

The object of the present disclosure is to create a speaking valve, which has a simple construction and can be produced inexpensively.

The object is achieved according to the present disclosure by means of speaking valve according to Claim 1. Further advantageous designs can be derived from the following description, the Figures, and the dependent Claims. The individual features of the designs described herein are not limited thereto, but instead can be combined with one another and with other features to obtain further designs.

A speaking valve for laryngectomized or tracheostomized patients is proposed. The speaking valve comprises a cover part, a housing part, and a filter. The cover part also comprises a closure part. The closure part and the cover part form a component of the valve. The closure part is advantageously fully disposed in an interior formed by the housing part.

The cover part further comprises an elastic material, which has, in particular, rubber-elastic properties, wherein the cover part that has the closure part of the speaking valve closes the filter at the distal side by means of deformation, in particular an indenting, of at least one region of the cover part toward the proximal side.

Advantageously, the cover part (with the closure part), filter and/or housing part can be separated from one another, such that in particular, the cover part or the filter is designed such that it can be replaced. The cover part, filter and housing part are thus separate components according to an advantageous embodiment.

The reset force needed when changing the speaking valve from a closed position necessary for speaking, to an open position, is preferably provided substantially, advantageously substantially entirely, preferably entirely, by a cover part made from an elastic material. As a result, otherwise necessary reset means, such as springs or the like, are advantageously eliminated. Because the filter is at most slightly compressed by the distal closure, in particular substantially only in a sub-region disposed above a valve seat provided by the housing part, preferably substantially only in part, more preferably not at all, its heat and moisture exchanging function remains as good as entirely intact, if not entirely.

In accordance with the present disclosure, the direction indications used in the present disclosure are to be understood in relation to the intended installation on the body, or on a tracheal cannula or a tracheostoma bandage. When a central axis and an orientation with respect to this central axis are referred to in the present disclosure, it should be assumed that the central axis is disposed in the center of the speaking valve. The speaking valve accordingly has a radially symmetrical design, in particular having a circular housing part, and thus has a center point at least on the housing part, when viewed from above, through which the central axis runs. The central axis runs through the speaking valve according to the present disclosure, parallel to an inner or outer contour, or outer wall, of the housing part. If a component or feature is referred to as being parallel to the central axis of the present disclosure, this also refers to the central axis as defined above, and a parallel alignment of the component thereto. If a vertical orientation is referred to in the present disclosure, in particular in relation to the cover part, in particular an outer edge thereof, this is likewise to be understood to mean a substantially parallel alignment in relation to the central axis. When a lateral arrangement is referred to in the present disclosure, in particular with regard to the cover part, in particular a lateral extension of the cover part over an outer contour of the housing part, this is to be understood to mean a substantially perpendicular alignment in relation to the central axis.

The term, "distal," in relation to a feature of the device according to the present disclosure, is understood to mean, as set forth in the present disclosure, an arrangement or use of said feature at a distance to, or facing away from, or lying opposite a tracheostoma bandage or a tracheal cannula, in general a skin surface of a person, in particular wearing such an attachment means for the device according to the present disclosure. A closure distal to the filter, i.e. a changing the closure part from an open position into a closed position, means that the filter is disposed entirely beneath the closure part, i.e. proximally. The term, "proximal," in relation to a feature of the device according to the present disclosure, is understood to mean, as set forth in the present disclosure, an arrangement or use of said feature close to, or facing, or adjacent to a tracheostoma bandage or a tracheal cannula, in general a skin surface of a person that wears, in particular, such an attachment means for the device according to the present disclosure.

"Integral" as set forth in the present disclosure, does not mean, for example, that the closure part and cover part must be made of the same material. They can be made, for example, of different materials, and bonded to one another, e.g. through adhesive, mechanical means, etc. In this case as well, the two parts collectively form a single component of the speaking valve according to the present disclosure, which can then be referred to as "integral," as set forth in the present disclosure.

The proposed speaking valve has the advantage that very few components are used to form the speaking valve. The speaking valve is composed substantially of three components, specifically the filter, the housing part and the cover part, which comprises the closure part, and thus forms a component together therewith. Moreover, the speaking valve according to the present disclosure has the major advantage that, due to the specific design of the closure part, whistling noises are prevented, in particular during inhalation, because a space between the closure part and the filter is enlarged, specifically, by the rising middle part. Furthermore, turbulences are caused in the space between the closure part and the filter through the design of the speaking valve, which enable a uniform moisturizing and heating of the respiratory air through a full exploitation of the capacity of the filter. Due to the special design of the closure part, inflow openings disposed in the housing part, in particular, can be kept small. Respiratory air is inhaled through these inflow openings, or discharged. The inflow openings can thus exhibit a height, in particular, parallel to a central axis of the speaking valve according to the present disclosure, which is quite low, such that ultimately, a relatively flat speaking valve according to the present disclosure can also advantageously be produced.

In a particularly preferred embodiment, the closure part has at least one lip element on the surface of the outer edge. The lip element is preferably formed on the surface as an extension of an outer wall of the outer edge of the closure part, which is disposed opposite an inner wall of the housing part. The lip element is preferably elastic. It preferably interacts with the valve seat of the housing part. Advantageously, the lip element improves a sealing effect of the closure part when it is changed into the closed position by exerting pressure on the at least one region of the cover part that is elastic, through its interaction with the valve seat, which is preferably formed by the housing part. The lip element is preferably formed as a closed ring, but numerous lip elements, e.g. one, two, three, four, five, six, seven, eight, nine, or more, can also be disposed on the surface of the outer edge of the closure part. If numerous lip elements are provided, these are preferably interrupted by short regions, wherein the lip element displaces material into this region in interacting with the valve seat, when moving the closure part into a closed position of the speaking valve, such that a substantially sealing effect can be obtained. The height of the lip element in relation to a height of the outer edge of the closure part, likewise determined parallel to the central axis of the speaking valve, is 2% to approx. 20% of the height of the outer edge, or its outer wall, preferably approx. 3% to approx. 15%, more preferably approx. 5% to approx. 12%, of the height of the outer edge of the closure part.

In a preferred embodiment, the outer edge of the valve part has an outer wall, which is disposed substantially parallel to an inner contour or an inner wall of the housing part. As a result, a reliable guidance of the closure part into the housing part can be obtained, when changing the speaking valve to the closed position and reset by the elastic material of the cover part to an open position.

The attachment region also preferably comprises a cavity into which an attachment projection of the cover part can engage. The cavity in the attachment region of the closure part is particularly preferably an opening or borehole passing through closure part. The attachment projection of the cover part is particularly preferably shaped like a nub, in particular a nub-like projection with a circumferential groove. The closure part is advantageously disposed in this groove, which has a height in the attachment region that corresponds approximately to that of the groove. The attachment projection is particularly preferably made of the same elastic material as the at least one region of the cover part that enables a closed position of the speaking valve through deformation thereof. The attachment projection furthermore preferably has a diameter that is large enough, on one hand, to close the hole or opening of the closure part in a sealing manner, and on the other hand, to provide sufficient stability through the elastic material that is preferably used, such that a reliable retention of the closure part on the inner surface of the cover part is ensured.

It is provided in one design, that the housing part comprises a distal valve seat. The closure part interacts with the valve seat when the speaking valve is actuated, in particular via its lower surface of the outer edge. Advantageously, the speaking valve and valve seat interact such that the valve closes. The actual valve is formed by the closure part and the valve seat. The valve seat is preferably disposed in the interior of the housing part, and is preferably disposed as a circumferential projection beneath or at the same height as a lower hole edge of the inflow openings in the housing part.

In a particularly preferred embodiment, the lower surface of the closure part interacts at least in part with the valve seat. Preferably, a surface portion of at least 50% of the surface interacts with the valve seat in the housing part. The lower surface of the outer edge of the valve part is disposed, particularly preferably, parallel to the surface of the valve seat. If at least one lip element is disposed on the lower surface of the outer edge of the closure part, this likewise interacts with the valve seat, preferably entirely, i.e. over the entire surface of the lip element, with the valve seat surface provided by the housing part. When a strong pressure is exerted by the user of the speaking valve, the lower surface of the outer wall of the closure part then also interacts with the valve seat, i.e. the seating surface provided by the valve seat. In a particularly preferred embodiment, the at least one lip element interacts with the valve seat.

In an advantageous embodiment, it is provided that the housing part comprises inflow openings distal to the valve seat. This has the advantage that an inflowing air during inhalation flows entirely through the filter disposed in the housing, before it flows further through the at least one outflow opening into, e.g., a tracheal cannula or the trachea. The valve seat is preferably disposed on the same plane as the distal end of the filter, but it can also be disposed above or below the distal end of the filter. When it is disposed below the distal end of the filter, the filter is compressed slightly, substantially in the excess part of the filter, when changing the speaking valve from an open position to a closed position. In a further design, it is provided that the valve seat is disposed such that it is distally spaced apart from the surface of the filter. A further variation provides that the valve seat is disposed in the housing, such that it is spaced apart from the distal end of the filter, such that when the speaking valve is closed, the piston of the filter is partially compressed. The, in particular partial, sealing of the filter during the closing procedure shall be explained in greater detail below.

In a particularly preferred embodiment, the at least one inflow opening has a height facing toward the central axis of the speaking valve according to the present disclosure that is basically equal to or less than a height of the outer edge or the outer wall, or potentially, the outer wall, including the at least one lip element, of the closure part. As a result, it is ensured that the closure part is also reliably guided inside the housing part in the region of the inflow openings, insofar as at least a region of the cover part is deformed when the speaking valve is operated by a person.

It is provided in another embodiment that the housing part comprises inflow openings, which can be closed by means of the closure part when actuating the speaking valve. In particular, the closure part is inserted into the housing such that when the speaking valve is actuated, the airflow through the inflow openings is at least partially blocked from inside the housing. The speaking valve is thus closed in this embodiment by alternative or collectively acting closure mechanisms: on one hand, the closure part at least partially blocks the airflow through the inflow opening. Furthermore, the closure part is equipped such that it interacts with the valve seat or the filter, when it is pushed into the housing part, such that the blockage of the airflow is carried out inside the housing. A further closure is provided when the closure part bears on the filter, in particular in the region of the lower surface of the outer edge of the closure part, and preferably extends beyond an outer circumference of the filter when it has been inserted, such that airflow through the filter is substantially prevented. This has the advantage that a reliable sealing of the speaking valve takes place. In the region of the closure part, in particular a central region, one or more openings can be provided, alternatively or additionally in the cover part and optionally, in the closure part as well, in order to allow air to flow through the valve. These are preferably closed when the valve is closed, in particular by a finger of the user.

According to a further embodiment, it is provided that the cover part is releasably disposed on the housing part. By way of example, different cover parts may be provided for a housing part, which have different material properties, e.g. in terms of rigidity or shape. The cover part may also exhibit different colors and embellishments, provided for decorative purposes, such that a variable design possibility is obtained for the speaking valve, and thus for the tracheostoma.

Another advantage of the exchangeability of the cover part is that when the material of the cover part becomes aged through use, accompanied by a constant deformation, the cover part can be replaced, wherein the housing and filter can remain in place. It is also advantageous that insofar as the cover part is releasably disposed on the housing, the filter can be easily removed from the housing and replaced.

In one variation of the speaking valve, it is provided that the cover part is disposed by means of a latching connection on the housing part. There are, however, other possibilities for a releasable connection, e.g. provided by one or more Velcro connections or adhesive connections. The latching connection can be created such that the cover part has at least one, two, three, four or more latching elements, e.g. in the form of latching lugs, which are disposed on an inner surface of the cover part dedicated to the lateral walls of the housing part. It can be provided thereby that the latching elements encompass an upper edge of the housing part in a region thereof in which the inflow opening are provided. Corresponding receivers, projections, or recesses, or even interruptions, can be provided on this edge, into which the at least one latching element of the cover part latches, or which said latching elements encompass. Conversely, corresponding latching elements could also be disposed in the distal end region of the housing part, e.g. latching lugs, which latch into corresponding holes, or encompass projections, which are disposed on the undersurface of the cover part.

In a particularly preferred embodiment, the cover part has at least one latching element disposed on its inner surface, which forms at least one at least partially circumferential groove. The at least one latching element is particularly preferably L-shaped thereby, seen in the cross section of the speaking valve, in a plane that runs through the central axis thereof. The groove is particularly preferably formed by a short leg of the L, and by a surface provided by the inner surface of the cover part. Seen in the cross section, the groove particularly preferably has a U-shape, or is semicircular or the like. In any case, an upper boundary of the groove is formed by a sub-surface of the inner surface of the cover part. A lower boundary of the groove is formed by the latching element. It is particularly preferred that precisely one latching element is disposed thereon, such that it runs along the circumference of the inner surface of the cover part. It may also be provided that some interruption elements are disposed in the groove, e.g. two, three, four or more, which can also be referred to as filler pieces in the groove. In this case, the cover part is designed such that it can be placed such that it fits precisely on a corresponding housing part, i.e. such that it is latched thereto. Accordingly, corresponding latching projections with cavities are provided in an upper edge of the housing part, wherein the width of the cavities corresponds approximately to filler elements in the groove formed by the latching element on the inner surface of the cover part.

The releasable connection between the cover part and the housing part is preferably designed such that no air can flow in or out through the connecting region between the cover part and the housing part. In a preferred embodiment, it is provided that three or four latching lugs, or one latching element forming a circumferential groove, are or is disposed on the inner surface of the cover part. The three or four latching lugs are disposed on a collar or bead, disposed on the inner surface of the cover part for obtaining a sufficiently secure connection, the dimensions of which, in particular the diameter thereof, correspond to the diameter of the housing part, and the upper edge of which basically covers the lateral walls of the housing part. The latching elements, or lugs, preferably engage in corresponding cavities on the upper edge of the cover part, or encompass projections provided there. The bead or collar, or the latching element, formed by at least one, at least partially circumferential, groove, as explained above, can be disposed spaced only slightly apart from an outer edge of the cover part. The cover part can be riveted or screwed to the housing part, however, or it can be connected to the housing part, for example, in the manner of a bayonet joint. Another variation provides that the cover part is screwed onto the housing part. Furthermore, one design provides that the cover part is attached to the housing part by means of a bayonet joint. Another variation may be provided, in which the cover part is glued or welded to the housing part.

The different adjustment possibilities, e.g. in terms of the elasticity of the material, in particular the rubber-elastic material, or the shape thereof, can affect the properties of the speaking valve. Thus, the material properties and the thickness of the material of the cover part, as well as the shape thereof, can have an effect on the reset force. In one design, it is provided that differently adjusted cover parts are provided, which are disposed on the housing part such that they can be exchanged, and can be used for different application purposes.

According to the present disclosure, the cover part is a least partially formed from an elastic material. Advantageously, the elastic material of the cover part is a rubber-elastic material. The elastic material of the cover part is preferably a linear-elastic material. In particular, organic rubber or synthetic rubber, or EPDM (ethylene propylene diene monomer) rubber may be used for the rubber-elastic material. It is also possible to use silicone materials, in particular medical silicone materials. Fundamentally, the rubber-elastic material of the cover part can be an elastomer, e.g. a thermoelastic elastomer having an olefin or urethane base, particularly preferably an at least partially cross-linked thermoplastic elastomer having an olefin base, a polyester elastomer, a thermoplastic copolyester, a styrene polymer, or a thermoplastic copolymer. Instead of a rubber-elastic material formed by a polymer, the cover part can be made at least in part from a linear-elastic material, in particular a metal having sufficient elasticity. Other materials providing sufficient elasticity can also be used. Particularly preferably, the cover part is made of an elastic, preferably rubber-elastic, material, and does not include any other materials. The cover part can have a uniform thickness thereby, although the thickness may be reduced, in particular in the region of the transition from a horizontal extension to a vertical extension of the cover part, and/or likewise in a region through which the user changes the speaking valve from the open position to the closed position and back by means of a finger.

In a preferred design, it is provided that at least one elastic region of the cover part functions as a reset element. According to one design, the elastic material of the cover part is a rubber-elastic material. If this is pressed inward, in order to displace the closure part proximally inside the housing, and to thus close the speaking valve, the inherent reset force of the rubber-elastic material causes the speaking valve to re-open as soon as the force to the cover part is reduced. Another design provides that the elastic material of the cover part is a linear-elastic material, e.g. a metal. The cover part can be composed of one or more materials. In particular, it is provided in one design that materials having different elastic properties are provided, and that, e.g., the closure part includes a different material, in particular a rigid, i.e. non-elastic material, or a less elastic material, than the cover part. It is particularly preferred thereby that the closure part is made, for example, of a silicone material, in particular a medical silicone, which has a greater stability, i.e. rigidity, than the material of the cover part. The cover part itself is preferably made of an elastic material, as described above. In another advantageous design, it is provided that the cover part, and thus the closure part as well, are made of an elastic material, preferably an identical elastic material. Preferably, the cover part can be produced with the closure part in a single-component injection molding process. When an identical elastic material is used, the elasticity of the cover part and the closure part can be affected, e.g., via the wall thicknesses or other mechanical means, e.g. beading or reinforcement stays, hollow chambers, etc., such that they exhibit different elasticity modules, despite being made of the same material.

Furthermore, one design provides that the closure part is made at least in part of a more rigid material than the cover part, i.e. a stiffer or less, or non-, elastic material, in particular in the region of the surface that interacts with the valve seat, in particular the lower surface of the outer edge of the closure part. The use of a rigid or more rigid material for the closure part has the advantage that this part does not become deformed, or only becomes insubstantially deformed, when it is guided through the housing part during the actuation. Thus, even when the user does not press on the center of the cover part, the speaking valve can be fully closed, because the closure part does not become deformed in a biased manner, or in a non-uniform manner, as it is forced into the housing part, thus resulting in an insufficient closure. In a further design, it is provided that the rigidity of the closure part is obtained, in particular, by means of the use of elastic or rubber-elastic solid materials, or is adjusted by these. The closure part can be formed as an integral part of the cover part, in particular from the same material. The closure part is preferably made of a material having a lower elasticity module than the cover part, thus from a more rigid material. The closure part is particularly preferably provided with at least one cavity on its surface facing the cover part, which can also be an opening or borehole, or at least a projection. Conversely, at least one projection or at least one cavity, preferably not in the form of an opening or borehole, is preferably provided on the undersurface of the cover part facing the closure part. The cavity and projection of the cover part and closure part interact, e.g. through a form or force fit, in particular through adhesive or mechanical latching or suchlike, such that an integral component, as set forth in the present application, is obtained, comprised of the cover part and closure part, which are connected to form a single part.

The cover part is advantageously designed in the manner of a hat or cap. This is to be understood as a design of the cover part, such that the cover part extends over the lateral walls of the housing part, at least in part, preferably entirely (i.e. on all sides). The extension over the lateral walls of the housing part advantageously takes place thereby in a direction substantially parallel to a skin surface of the body, or substantially perpendicular to the central axis of the speaking valve according to the present disclosure. The extension over the lateral walls of the housing part is also preferably vertical, i.e. in the direction of the vertical extension of the housing part from its proximal end to its distal end, or substantially parallel to the central axis of the speaking valve according to the present disclosure. The vertical extension preferably takes place over a sub-length of the vertical extension of the housing part. The cover part can also have openings in the region extending over the lateral walls of the housing part, in particular in the form of slots. Openings can also be disposed in the deformation region of the cover part as well, in particular precisely one opening, which is closed by the user when changing to the closed position. It is provided in one design that when the closure part, as is possible, is not fully or partially connected at its upper surface, which faces the undersurface of the cover part, to the undersurface of the cover part, it is somewhat spaced apart therefrom, in particular, e.g. by a type of attachment cross, the intersection of which is provided with at least one cavity or at least one projection for attaching it to the undersurface of the cover part. The cover part can have at least one projection or at least one cavity on its undersurface, which interacts with the corresponding means of the closure part. By way of example, the projection can be in the form of a pin or rod, and the cavity can be a blind hole, which is preferably adapted to the projection. A form and/or force fitting connection is preferably obtained between the cover part and the closure part.

The attachment region of the closure part comprises, in addition to a cavity, preferably formed as an opening or borehole, a reinforcement encompassing this cavity, which can be in the form of a bead, for example. The reinforcement can be referred to as a material thickening, or material reinforcement. In particular, an inner wall of the cavity, or opening, is designed such that it engages in a circumferential groove disposed on an attachment projection of the cover part in a form and/or force fitting manner.

Advantageously, the cover part has a height, from the proximal side to the distal side, and thus parallel to the central axis of the speaking valve according to the present disclosure, when it has not been assembled, i.e. is released from the housing part, corresponding to at least 10% to approx. 80%, preferably approx. 15% to approx. 65%, more preferably approx. 25% to approx. 30%, more preferably approx. 30% to approx. 48%, of a height of the housing part. In the assembled state, i.e. when the cover part is disposed on the housing part, preferably latched thereto, a part of the cover part extends vertically over the housing part, and particularly preferably, a vertical covering of the at least one inflow opening in the housing part is obtained, at least to 50%, preferably at least 80%, more preferably at least 90%, and even more preferably, entirely. The above percentages are to be understood for a view of the speaking valve according to the present disclosure, with the cover part disposed on the housing part, in a direction along the central axis, parallel thereto. If the speaking valve is viewed from the side, the at least one inflow opening is preferably nearly entirely covered by the cover part, i.e. there is still a gap of an inflow opening visible to an observer viewing the speaking valve according to the present disclosure from the side.

The height of the cover part from the distal side to the proximal side is determined, on one hand, by a lower surface of the edge, which can also be referred to as a cervical edge, and on the other hand, by the distal surface thereof, that is furthest away from the tracheostoma.

Insofar as the term, "approx." is used in the framework of the present disclosure, this is understood to relate to a tolerance range regarded as typical by the person skilled in the art in the present field, in particular a tolerance range of ±20%, preferably ±10%, more preferably ±5%, in each case in relation to the value or range of values in question.

In a preferred embodiment, the cover part extends over the housing part both laterally as well as vertically. The cover part also preferably comprises a cervical edge. The cervical edge, i.e. the lower surface of the edge of the cover part facing the throat of a wearer of the speaking valve according to the present disclosure, is preferably rounded, such that it does not irritate the skin when it comes in contact therewith when the user moves.

In particular, the cover part has a round, oval, or other rounded, or a rectangular shape, when viewed from the side, wherein with an angular shape, the corners are advantageously rounded. Advantageously, all of the edges of the cover part are rounded, in order to avoid injuries or skin irritation in particular. The lower surface of the edge of the cover part, which extends horizontally and vertically over the housing part, in particular an outer contour thereof, advantageously lies at approximately the same height of a lower opening edge of the at least one inflow opening.

The advantage with any of the features described above in conjunction with the design of the cover part, is a guidance of the air during inhalation along the throat, such that the air is pre-heated before it reaches the interior of the speaking valve, and in particular the filter. Depending on the design of the cover part, in particular with regard to the placement of the cervical edge closer to the lateral walls of the housing part, or at a greater distance thereto, as well as by the placement of the cover part with the cervical edge, such that the cervical edge is closer to or further from the throat of the user, the volume of the airflow that is to be received, as well as by pre-heating thereof, can be affected.

It is particularly advantageous when the cover part does not have a distal opening, in particular in a central region, which enables air to pass through the filter from the distal side to the proximal side. The housing part preferably comprises one or more inflow openings in a lateral wall thereof. As a result, it is ensured that the air is guided substantially along the throat before it enters the housing part. Alternatively or additionally, it can also be provided that the cover part has at least one distal opening, in particular in a region facing the interior of the housing part. At least a part of the inhaled air can pass directly into the housing, or through the filter, through the at least one distal opening, such that the air can pass into the trachea or into the trachea cannula after it has been moisturized and heated.

In a further variation of the speaking valve, it is provided that the filter is disposed in the housing part with an excess. The filter preferably exhibits no play in the housing according to one design. This prevents inhaled and exhaled air from bypassing the filter. Furthermore, the filter fitted in this manner has the advantage that it is not displaced in the housing by the alternating air pressures. It is, however, also possible to dispose the filter in the housing such that a gap is formed between the outer walls and the inner walls of the housing. The filter can be retained by a housing part, through adhesive or suchlike, or it can be retained, for example, only by the squeezing fit. Retention means can also be disposed on the inner walls of the housing part, which press into the filter material. These can be designed as truncated cones, for example. Any other design of the retention means is also possible, however, as long as they ensure that the filter is retained in the housing part.

A major advantage of the proposed speaking valve is that the filter is not, or is only partially, compressed when the speaking valve is closed, in particular due to a part of the filter possibly extending over the valve seat. The compression of the filter in the artificial noses or speaking valves known from the prior art has the disadvantage that the filter is wringed out, and thus loses its moisture. Furthermore, there is fundamentally the risk of the filter material being pushed into the tracheal cannula, and in the worst case, being inhaled by the user.

It is provided in one embodiment that the filter is partially compressed by the actuation of the speaking valve. A partial compression of the filter may take place intentionally or on purpose during a closing in one design due to the tolerances of the speaking valve. The speaking valve is designed such that a compression is provided of approx. 0 or 1% by volume to approx. 50% by volume, in particular approx. 0 or 1% by volume to approx. 35% by volume, more preferably approx. 1% by volume to approx. 50% by volume, more preferably approx. 1% by volume to approx. 35% by volume, particularly preferably approx. 1% by volume to approx. 25% by volume. The compression can be adjusted, for example, by the cover material, or by the geometry of the cover. As a result, it is indicated to the user by the normally applied force, e.g. approx. 5 N to approx. 15 N, when it is no longer necessary to press further inward. If the user attempts to push the cover part further inward, this normally leads to discomfort through the pressure applied to the tracheostoma, or the surrounding tissue, or the tracheal cannula. The speaking valve is designed such that it already closed before the normally applied force of, e.g., approx. 5 N to approx. 15 N has been reached. The adjustment of the compression of the filter is advantageously set through the placement of the valve seat in the housing part, in particular at a specific height inside the housing part. It is provided in a further design that a compression of the filter is limited by means of a counter-bearing disposed in or on the housing part. Preferably, the closure part can only pressed into the speaking valve as far as the counter-bearing. The provision of a counter-bearing prevents the filter from being pushed through, into the tracheal cannula, and thus from being inhaled. Furthermore, a wringing out of the moisture in the filter is minimized or prevented by the limited compression. The counter-bearing can be implemented, by way of example, as a rod or wall, which extends from the proximal side to the distal side through the filter, and is disposed in some form on the housing. Another possible design provides that the counter-bearing is designed as an at least partially circumferential edge, which is preferably not identical to the valve seat.

Moreover, the present disclosure relates to a closure part, as described above in conjunction with the speaking valve according to the present disclosure.

Further advantageous designs can be derived from the following drawings. The illustrations depicted therein are not to be interpreted as limiting, but rather, the features described therein can be combined among themselves and with the features described above to obtain further designs. Moreover, it should be noted that the reference symbols given in the description of the Figures do not limit the scope of protection for the present disclosure, but refer only to the exemplary embodiments indicated in the Figures. Therein:

DETAILED DESCRIPTION OF THE INVENTION

Figure 1:
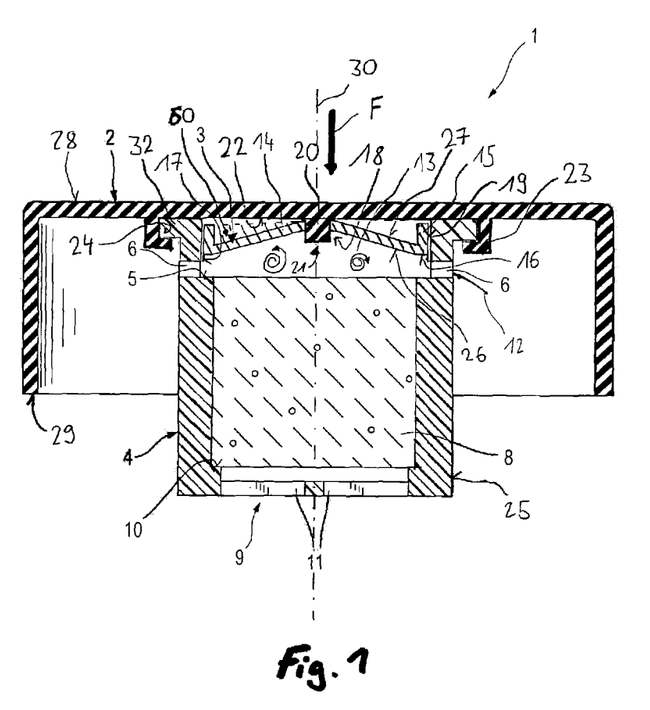
FIG. 1 shows a speaking valve in a first embodiment, in a side view, in the unactuated state.

FIG. 1 shows a speaking valve 1 for laryngectomized or tracheostomized humans in a sectional view in a first embodiment, having a cover part 2, a housing part 4 and a filter 8. The cover part 2 comprises a circular or disk-shaped closure part 3, which is connected to the cover part. In the design shown here, the cover part 2 is made entirely from an elastic material. The cover part 2 is disposed on the distal end of the housing part 4. Preferably, a latching connection is provided for attaching the cover part 2 to the housing part 4. For this, latching elements 23 are formed on an inner surface 22 of the cover part 2, having a basically L-shaped cross section. Preferably, exactly one, annular latching element 23 is provided, running circumferentially on an inner surface 22 of the cover part 2. Together with an inner surface of the inner surface 22 of the cover part 2, this forms a circumferential annular groove 24 with a cross section in the shape of a horizontal U. A latching projection 32 of the housing part 4 disposed on an upper edge 34 of the housing part 4 (see FIG. 5, for example) can engage in this circumferential annular groove 24. It is particularly preferred thereby that the latching projection 32 is formed as a circumferential projection on the upper edge 34 of the housing part 4, disposed on its outer wall, but it can also be formed, particularly preferably, as just a partially annular latching projection 32, such that two, three, four, or more such, partially circular latching projections 32, disposed circumferentially on the outer wall of the upper edge 34 of the housing part 4, may be provided, which engage in the annular groove 24. Preferably a form and/or force fitting connection is obtained between the cover part 2 and the housing part 4 by the latching. In an alternative design, it is provided that the cover part 2 is connected by clamping or adhesive to the housing part 4 through a secure seating of the closure part in the housing part 4. Inflow openings 6 are provided, proximal to the closure part 3, in the lateral walls of the housing part 4, which allow air to flow in. Outflow openings 9 are provided at the proximal end of the housing part 4, which enable an outflow of the inhaled air during inhalation, into the tracheal cannula or the tracheostoma. A valve seat 5 is formed by the lateral walls of the housing part 4 as a circumferential projection in the form of a constriction of the cross section.

The filter 8, which is disposed such that it fits precisely in the housing part 4, moisturizes the inflowing air, before it reaches the tracheal cannula or the tracheostoma. A filter seat 10 is disposed in the proximal end of the housing part 4, which prevents the filter from sliding into the tracheal cannula or the trachea, respectively In an alternative embodiment, a filter seat 10 can be omitted, and instead, a support cross 11 is provided, exclusively for preventing a sliding of the filter 8 through the at least one outflow opening 9, which has three, four, five or more support arms. The filter 8 can be in direct contact with, or bear on, a surface of the support cross 11 facing it. In the embodiment shown here, a support cross 11 is provided, which likewise prevents the ingress of foreign bodies, in particular the filter 8, into the trachea.

The cover part 2 also has an attachment projection on its inner surface 22, in the form of an attachment nub, which engages in a cavity 21 of the closure part 3 formed as an opening in the manner of a borehole, and as a result, retains the closure part 3 on the inside of the cover part 2, above the filter 8 in the housing part 4. The closure part 3 has an outer edge 15 with a lower surface 16 and an upper surface 40 (see FIG. 10), wherein a lip element 17 is disposed on the lower surface 16, wherein the lip element 17 is disposed on the lower surface 16 in an extension of an outer wall 19 of the outer edge 15. The closure part 3 is circular or disk-shaped, as can be derived in particular from FIGS. 10 and 11. An attachment region 18 of the closure part 3, defined in particular by the cavity 21, is also provided, which can have a material bead 42, encircling the cavity 21 in particular (see FIG. 10), in particular a bead-shaped material thickening, in order to ensure a secure retention of the closure part 3 on the attachment projection 20 of the cover part 2.

Starting from the circular circumferential lower surface 16 of the closure part 3, extending as far as the attachment region 18, the closure part 3 has a middle part 14, having a lower rising surface 26 and an upper surface 27, wherein the latter faces the inner surfaces 22 of the cover part 2. The lower, rising surface 26 faces toward the housing interior, and in particular the filter 8. The middle part 15 rises from the lower surface 16 of the outer edge 15 to the attachment region 18, i.e. in particular at an angle to the central axis 30 of the speaking valve 1. As a result, a space 13 is formed between the closure part 3, in particular its lower rising surface 26 of the middle part 14, and a surface of the filter 8, in which turbulence is formed in the air inhaled through the inflow openings 6, such that the air passes in a uniform manner through the filter 8 during inhalation, i.e. the air experiences a uniform moisturizing and heating. Moreover, the space is configured, due to the specific design of the closure part 3, such that air flowing inward through the inflow openings 6 is inhaled without making a whistling noise. The inflow openings 6 are particularly preferably disposed on a plane of the housing part 4 in its interior. The inflow openings are interrupted by webs, which connect the lower housing part to the upper edge 34 of the housing part 4. As a result, a sufficient stability of the housing part 4 is obtained, as can also be derived from FIGS. 5 to 7.

The lower surface 16 of the outer edge 15 of the closure part 3, as well as the lip element 17, interact with the valve seat 5 when the speaking valve 1 is changed from the open position to the closed position. When a force F is applied in the direction of the arrow shown in FIG. 1, via a surface 28 of the cover part 2, the cover part 2 made of an elastic material becomes deformed, and thus enables an interaction of the lower surface 16 of the closure part 3, or the lip element 17, with the valve seat surface of the valve seat 5. Because of the lip element 17, a substantially airtight sealing of the valve takes place in such a closed position, such that no air can be inhaled or exhaled through the inflow openings 6. If no lip element 17 is provided, the surface 16 and the valve seat surface of the valve seat 5 are preferably coplanar, such that a full sealing is provided. The closure part 3 is particularly preferably made of a medical silicone, and exhibits a certain stiffness, but also a certain elasticity, such that, due to this elasticity, in particular of the lip element(s) 17, the sealing effect is reinforced when the speaking valve 1 according to the present disclosure is changed from the open position to the closed position. The housing part 4, in contrast, is made from a hard, rigid plastic material, which has only a limited elasticity, if any.

A region of the closure part 3 is indicated by the reference numeral 60, which lies above the upper surface 27 of the middle part 14 of the closure part 3. It should be clear therefrom, that this region 60 can also be filled, i.e. the closure part 3 can be filled up to this level, which is determined by the upper surface of the material bead 42 of the outer edge 15, i.e. which then depicts in this case a circular disk with a cavity 21 in the middle, toward which a lower, rising surface 26 of the middle part 14 then extends. The closure part 3 can be referred to as conical.

The cover part 2 has a lower surface 29 in the region that extends vertically over an outer contour of the housing part 4. Moreover, the cover part 2 extends horizontally, i.e. perpendicular to the central axis 30, over an outer contour of the housing part 4. As a result, air can be inhaled through the inflow openings 6, as indicated by the arrow 12, wherein the inhaled air is pre-heated due to the proximity of the lower surface 29 to a skin surface of the wearer of the speaking valve 1. FIG. 1 shows just one possible design for the cover part 2 thereby. It can also be provided, in particular, that the lower surface 29 of the cover part 2 ends basically at the height of the valve seat 5, which preferably corresponds to a lower edge of the inflow opening 6. Sufficient pre-heating of the respiratory air is also obtained through this. As a result, the speaking valve 1 can also have a very small construction in particular, which represents a special advantage. The inflow openings 6 can be formed with a reduced height, due to the specific design of the closure part 3, which prevents whistling noises, preferably a height that is equal to or somewhat shorter than the height of the outer walls 19 of the outer edge 15 of the closure part 5. As a result, it is ensured that the closure part 3 is always guided securely in the interior of the housing part 4, regardless of whether the speaking valve is in the open position or closed position.

Figure 2:
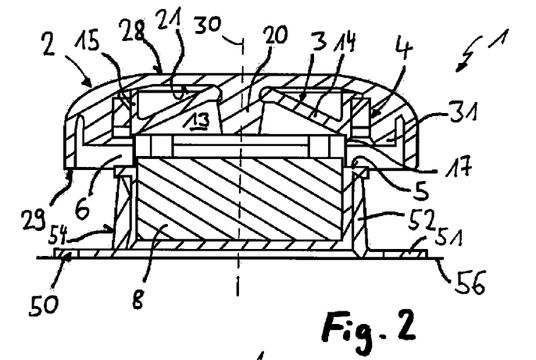
FIG. 2 shows a speaking valve in a second embodiment, in a sectional view, in the unactuated state, disposed on a tracheostoma bandage.

FIG. 2 shows an alternative embodiment of a speaking valve 1 according to the present disclosure, in a sectional view. In this, a surface of the filter 8 does not end at a valve seat surface of the valve seat 5, in differing from the embodiment according to FIG. 1, but instead extends beyond it distally. As a result, when the speaking valve 1 according to FIG. 2 is changed from an open position to a closed position, the closure part 3 interacts at the lower surface 16 of the outer wall 15 with the valve seat 5, at least in part, in particular in the region of the lip element 17, wherein the filter 8 is slightly partially compressed. As a result, an additional elastic effect is obtained when the closing valve is returned from the closed position to the open position. The filter 8 is typically made from an open cell foam material, which exhibits a certain elasticity, and thus a certain resilience, and thus supports the cover part 2 in its resilience, due to the use of an elastic material.

Apart from this, with the embodiment according to FIG. 2, in contrast to that according to FIG. 1, a lower surface 29 of the cover part 2 ends at approximately the height of the valve seat surface of the valve seat 5, as is already described in conjunction with the embodiment according to FIG. 1 in a first alternative. The latching element 23 of the cover part 2, disposed on the inner surface 22 thereof, has a different design. The section according to FIG. 2 shows a cut through filler elements 31 thereof, which can be readily discerned, in particular, in FIG. 8. The circumferential groove 24 of the cover part 2, formed by the latching element 23 and a sub-surface of the inner surface 22 of the cover part 2, is not continuously circumferential thereby, but only partially circumferential, interrupted by a total of four filler elements 31. A precise fit of the cover part 2 to the housing part 4 is necessary for this.

Figure 5:
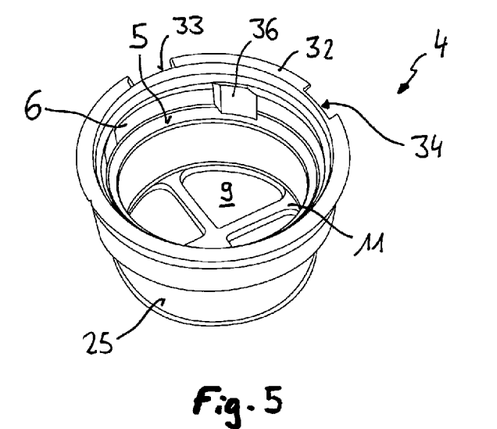
FIG. 5 shows a housing part for use on a speaking valve according to the present disclosure, in a perspective view.
Figure 6:
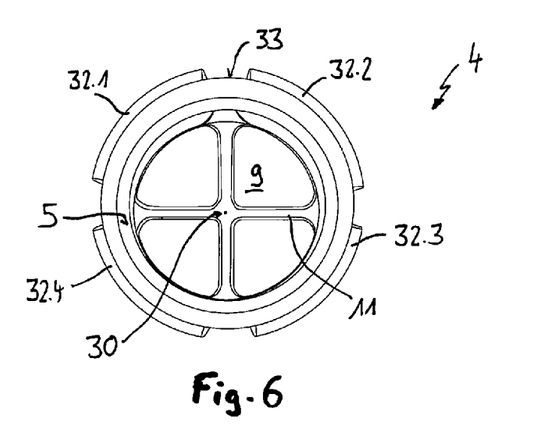
FIG. 6 shows the housing part according to FIG. 5 in a top view.
Figure 7:
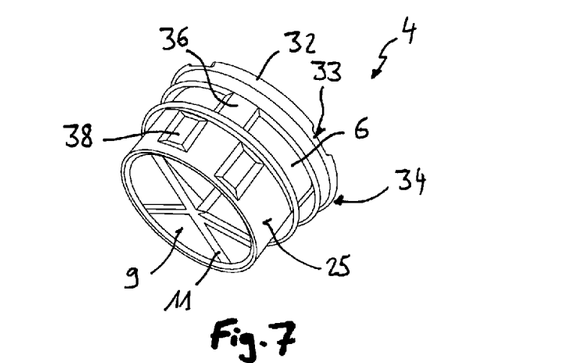
FIG. 7 shows the housing part according to FIG. 5 in a perspective view, diagonally from below.

As can be derived in particular from FIGS. 5 to 7, the housing part 4 has four latching projections 32.1 to 32.4 for this, which engage in the corresponding sub-regions of the annular groove 24, which has only a partially annular circumferential design.

The attachment projection 20 has a nub-like design with an encompassing annular groove, in which the attachment region 18 of the closure part 3 can engage. A secure placement of the closure part 3 on the inner surface 22 of the cover part 2 is enabled by the somewhat thickened design of the attachment projection 20, in conjunction with the elasticity of the material of the cover part 2.

As with the embodiment according to FIG. 1, the cover part 24 is made of an elastic material, while in contrast, the closure part 3 is made from a significantly more rigid, i.e. sturdy, material than the cover part 2. The closure part 3 nevertheless exhibits a certain elasticity, in order to obtain the best possible sealing effect when changing the speaking valve 1 to the closed position through interaction with the valve seat surface of the valve seat 5.

A tracheostoma bandage 50 is also shown in the embodiment in FIG. 2, in which the housing part 4 of the speaking valve 1 can be accommodated in a receiver 52 having an outer wall 54. The receiver has a base plate 51. The tracheostoma bandage 50 has, at the proximal side, an adhesive strip 56, in particular having an annular design, disposed on an undersurface of the base plate 51, by means of which it can be attached to the skin of a wearer. Alternatively, the speaking valve according to FIGS. 1 and 2 can also be accommodated in a tracheal cannula, which encompasses the outer walls 25 of the housing part 4 with its receiver.

Figure 3:
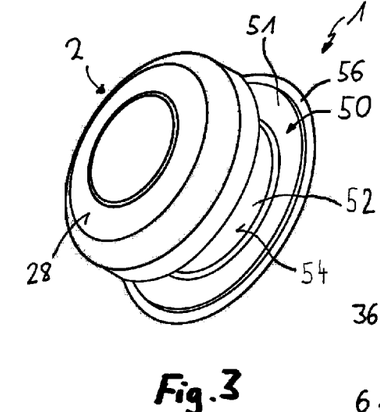
FIG. 3 shows the speaking valve according to FIG. 2, in a perspective view, diagonally from above.
Figure 4:
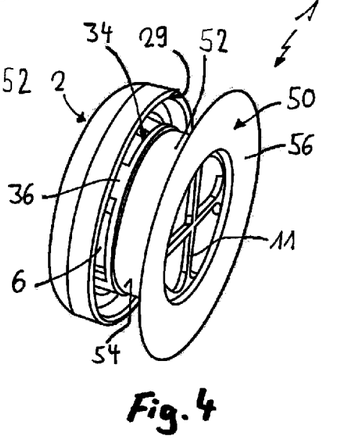
FIG. 4 shows the speaking valve according to FIG. 2, in a perspective view, diagonally from below.

FIGS. 3 and 4 show perspective designs of the second embodiment according to FIG. 2. In particular, the design of the support cross 11 that supports the filter 8 can be seen in FIG. 4. In contrast to the embodiment according to FIG. 1, the embodiment according to FIGS. 2 to 4 does not have a filter seat 10, and the filter 8 is retained by the support cross 11, preventing it from slipping into the trachea during respiration.

FIGS. 5 and 7 show the housing part 4, as can be used, for example, in the second embodiment according to FIGS. 2 to 4 of the speaking valve 1 according to the present disclosure. This has a total of four inflow openings 6, which are interrupted by a total of four webs 36, which connect a lower part of the housing part 4 with the upper edge 34 thereof. A total of four latching projections 32.1 to 32.4 are disposed on the upper edge 34, which can interact with the at least partially circumferential annular groove 24 of a cover part 2, as described above. The design of the support cross 11, with the total of four support arms, and four discharge openings 9 formed in accordance therewith, can also be readily discerned therein. The valve seat 5 forms a valve seat surface due to a cross section constriction of the housing part 4. Cavities 33 are disposed between the four latching projections 32.1 to 32.4. It may be provided, however, that these are omitted, for example, i.e. only one circumferential latching projection 32 is formed. Latching aids 38 can also be seen in FIG. 7, which serve for, or facilitate, the accommodation of the speaking valve according to the present disclosure in a tracheostoma bandage 50, as shown in FIGS. 2 to 4, or a tracheal cannula. These are accommodated in the housing walls 25 of the housing part 4.

Figure 8:
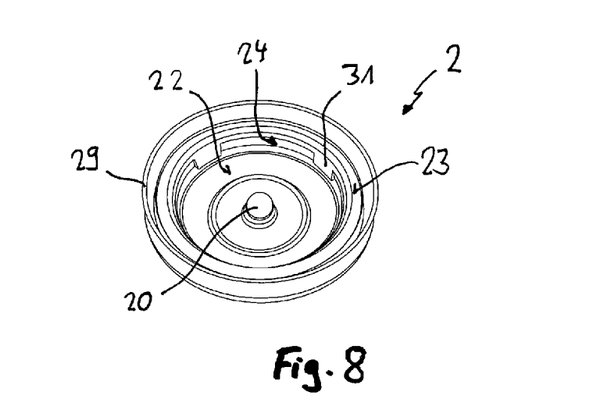
FIG. 8 shows a cover part for use in a speaking valve according to the present disclosure, in a perspective view, rotated upward in comparison to an assembled position of the cover part on a housing part.
Figure 9:
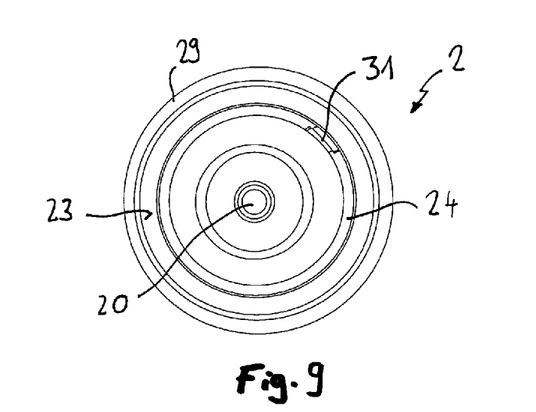
FIG. 9 shows a top view onto the cover part according to FIG. 8.

FIGS. 7 and 8 show a cover part 2, like that which can be used in the speaking valve 1 according to the present disclosure, in particular with those in accordance with the second embodiment according to FIGS. 2 to 4. The cover part 2 shown therein is designed such that it has an annular groove 24, which has only a partially circumferential annular design, because it is interrupted by filler elements 31, there being a total of four, such that the cover part 2 shown therein must be disposed such that it fits precisely on a housing part 4 according to FIGS. 5 to 7.

Figure 10:
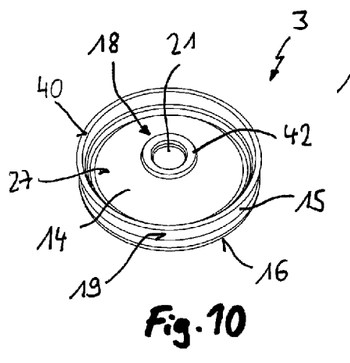
FIG. 10 shows a closure part 3 according to the present disclosure, for use in a speaking valve according to the present disclosure, in particular one such as according to FIGS. 1 to 4, in a perspective view.
Figure 11:
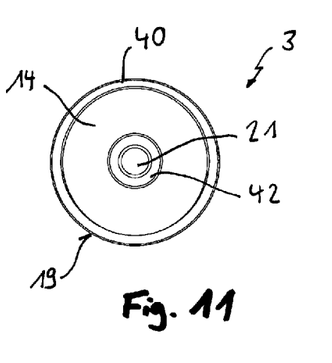
FIG. 11 shows a top view onto the closure part according to FIG. 10.

FIGS. 10 and 11 show a closure part 3 according to the present disclosure, as it can be used, in particular, in a speaking valve 1 according to FIGS. 1 to 4. An attachment region 18 can be clearly distinguished, having a cavity 21, encompassed by a material bead 42. Moreover, the closure part 3 has an outer edge 15, with a lower surface 16 and an upper surface 40, as well as a middle section 14, rising from the lower surface 16 to the attachment region 18. The middle section 14 forms an upper surface 27 and a lower surface 26 thereby, wherein the region defined as such can also be filled above the upper surface 27 to the upper surface 40 of the outer edge 15 and toward the material bead 42, as is indicated in principle by the reference symbol 60 in FIG. 1. The outer edge 15 has an outer wall 19, which serves, in particular, for a secure guidance of the closure part inside a speaking valve according to any of the exemplary embodiments 1 to 4, when changing from an open position to a closed position, and from the closed position back to the open position.

In a simple manner, a secure sealing of the speaking valve 1 is obtained through the specified measures, but also individually by each measure in and of itself. A reset force determined by the selection of the material, the shape and the cover part, and can be adjusted. If the force to the cover part is released, or the user releases the cover part, this reset force re-opens the valve.

The invention claimed is:

1. A speaking valve for laryngectomized or tracheostomized patients, the speaking valve comprising: a cover part, a housing part, and a filter disposed in the housing part, wherein the cover part includes a closure part disposed on an inner surface thereof, facing toward the filter, wherein the cover part also includes an elastic material, wherein the closure part closes the speaking valve at an end distal to the filter by deformation of at least one region of the cover part, wherein the closure part has a circular design with a lowermost outer edge, an ascending middle part continuously rising from the lower most outer edge portion to a highest most inner attachment projection extending from the cover part and arranged at a central axis of the housing part.

2. The speaking valve according to claim 1, wherein the lowermost outer edge portion of the closure part further comprises an upwardly angled lip element.

3. The speaking valve according to claim 1, wherein the outer edge has an outer wall, which is disposed parallel to an inner contour of the housing part.

4. The speaking valve according to claim 1, wherein an upper most inner edge of the closure part comprises a cavity, in which the attachment projection of the cover part can engage.

5. The speaking valve according to claim 2, wherein the housing part comprises a distal valve seat, wherein the closure part interacts with the valve seat when the speaking valve is actuated.

6. The speaking valve according to claim 5, wherein the lowermost outer edge of the closure part interacts at least in part with the valve seat.

7. The speaking valve according to claim 5, wherein the angled lip element interacts with the valve seat.

8. The speaking valve according to claim 1, wherein the housing part comprises at least one inflow opening.

9. The speaking valve according to claim 8, wherein the at least one inflow opening has a height in the direction of the central axis of the valve, which is basically equal to or less than the height of the outer edge of the closure part.

10. The speaking valve according to claim 1, wherein the cover part is releasably disposed on the housing part.

11. The speaking valve according to claim 1, wherein the cover part is disposed by means of a latching connection on the housing part.

12. The speaking valve according to claim 1, wherein the cover part has at least one latching element on its inner surface, which forms at least one at least partially circumferential groove.

13. The speaking valve according to claim 1, wherein at least one elastic region of the cover part functions as a reset element.

14. The speaking valve according to claim 1, wherein the closure part is made of a material that is more rigid than the cover part.

15. The speaking valve according to claim 1, wherein the cover part extends at least in part over the outside of the housing part.

16. The speaking valve according to claim 1, wherein the cover part extends over the housing part laterally and vertically.

17. The speaking valve according to claim 1, wherein the filter is disposed in the housing part with a interference fit or transition fit.

18. The speaking valve according to claim 1, wherein the filter is partially compressed by the actuation of the speaking valve.

* * * * *